United States Patent [19]
Wajaroff et al.

[11] 3,975,515
[45] Aug. 17, 1976

[54] REDUCING THE ALKALI CONCENTRATION IN HAIR TREATING COMPOSITIONS

[75] Inventors: Theodor Wajaroff; Eugen Konrad, both of Darmstadt, Germany

[73] Assignee: Wella AG, Darmstadt, Germany

[22] Filed: Sept. 30, 1974

[21] Appl. No.: 510,846

[30] Foreign Application Priority Data
Sept. 29, 1973 Germany............................ 2349050

[52] U.S. Cl............................. 424/72; 8/10.2; 424/70; 424/71; 424/DIG. 2
[51] Int. Cl.² ............................................ A61K 7/09
[58] Field of Search .................. 424/61, 70, 71, 72, 424/DIG. 2

[56] References Cited
UNITED STATES PATENTS
3,025,218  3/1962  Strain ................................. 424/72
3,252,866  5/1966  Sheffner ............................. 424/71
3,470,887  10/1969  Kremer .............................. 424/72

FOREIGN PATENTS OR APPLICATIONS
1,144,440  2/1963  Germany ............................ 424/72

OTHER PUBLICATIONS
The Merck Index, Merck & Co. Rahway, N. J. 8th Ed. 1968, pp. 184, 494.

*Primary Examiner*—Leonard Schenkman
*Assistant Examiner*—A. P. Fagelson
*Attorney, Agent, or Firm*—Michael J. Striker

[57] ABSTRACT

Process for reducing the alkali concentration in alkaline reactive cosmetic preparations which comprises the step of adding to such a preparation, shortly before its use, at least one alkali-cleavable organic compound having ester and/or halogen groups in its molecule and which is capable on cleavage to form an acid. The invention also includes the agents suitable for carrying out the aforesaid process.

6 Claims, No Drawings

REDUCING THE ALKALI CONCENTRATION IN HAIR TREATING COMPOSITIONS

This invention relates to a process and to an agent for gradually decreasing the alkali concentration in alkaline reactive cosmetic preparations.

Numerous cosmetic preparations are made up to provide an alkaline medium so that they contain large amounts of free alkali. This is the case for instance for oxidative hair dyeing agents which contain hydrogen peroxide and free alkali. There additionally belong to this group, the permanent waving agents which normally have a content of a mercaptocarboxylic acid salt and a free alkali. The alkali has the ability to swell the hair and skin and to thereby impart an absorbability for certain substances. Many substances used in formulating cosmetics as for instance the thioglycolates, sulfides, oxidative dyes and hydrogen peroxide display only in the alkaline pH range their maximum activity. Strong alkali is additionally able to soften keratin through splitting of S—S bridges so that for this reason many hair straighteners contain alkali lyes while in many hair shaping agents and hair colorants, alkalis such as ammonia, ammonium bicarbonate, ammonium carbonate or monoethanolamine are used. Further there are included in this aforesaid group of agents also the agents used for blonding hair which normally contain ammonia, sodium phosphate or sodium silicate. Oxidation hair dyes and blonding agents are generally treated before use by an addition thereto of hydrogen peroxide. Furthermore, there are used in different skin treatment agents, as for example cuticle removers, alkali lyes or other alkaline agents such as for instance trisodiumphosphate.

The aforedescribed cosmetic preparations are conventionally, in use, applied onto the hair or the skin and allowed to act thereon for a certain working period. According to the condition of the hair or skin to be treated, the working time required for the treatment can vary considerably. With longer time, there is increased in increasing measure the dangers of an overstressing or loading with the agent and therewith of resultant injuries to the hair and skin. This is particularly the case when the working period because of inadvertence or negligence of the operator is allowed to last too long. The art has always recognized the aforesaid problems and has made numerous attempts to reduce the hair and skin injuries brought about by treatment with cosmetics as has been above set out. These attempts have not, however, to date proved entirely successful.

In accordance with the invention a process and means has now been found whereby the aforesaid disadvantages associated with the use of alkaline reacting cosmetic preparations can be substantially reduced or eliminated. The invention comprises adding shortly before its use, to a cosmetic preparation, at least one alkali cleavable organic compound having ester and/or halogen groups in its molecule which is able as a result of the cleavage to form an acid and which may simultaneously have a reducing effect. Through the addition of these compounds to the cosmetic preparation, the activity of the cosmetic preparation can be regulated and further, through the choice of type and amount of additive, the concentration of the alkali can be decreased during the working period gradually down to the desired level. In preparations which additionally contain a mercapto compound or hydrogen peroxide, there can be through the addition in accordance with the invention also simultaneously be obtained a gradual decrease in the concentration of these latter agents.

In the process of the invention, there can be used as additives cleavable compounds in their pure form or in a suitably compounded form, for instance in admixture with at least one of a perfuming oil, wetting agent, solvent, adsorption agent or dyestuff. Thus for example the cleavable compound in the case that a liquid cleavable compound is involved can be bound to an adsorption agent such as colloidal silicic acid and then used as a powder or in the case where the compound is soluble in water only with difficulty there may be used a suitable solvent therefor such as an alcohol or a wetting agent such as octylphenol oxyethylated with 20 mols ethyleneoxide. Further the cleavable compound can be used following the conventional techniques in a microencapsulated form.

The cleavable compound can be used alone or in the form of mixtures thereof.

The acids which are gradually set free in carrying out the process of the invention are neutralized with a corresponding portion of the alkali present in the cosmetic preparation. Acids which simultaneously have a reducing effect, as for instance alpha-carbonyl carbonic acids react additionally with the hydrogen peroxide present in many of the preparations and serve thereby to reduce not only the alkali content but also the concentration of hydrogen peroxide in the preparation. Thus for instance, ethyl pyruvate through alkali saponification is converted into pyruvic acid which is then available to provide this duplicate effect. When heretofore a reduction of the alkali and a simultaneous reduction of the hydrogen peroxide concentration was to be effected during the working period, it was necessary in the treatment of the hair to effect a corresponding dilution of the alkaline preparation present on the head by addition of water thereto. This manner of proceeding has proved most unsatisfactory as for instance in the case of a hair dye, not only is there then effected a dilution of the alkali but of the dyestuff too so that the required concentration thereof is not present.

In carrying out the process of the invention, the alkali cleavable additive is used in an amount of about 1–10 wt. % based on the amount of the cosmetic preparation. It is to be understood that in carrying out the invention the amounts of additive used are adjusted in accordance with the desired treatment conditions and results to be achieved.

The alkaline cleavage of the ester and/or halogen group containing cleavable compound is favored by application of some heat. In the case of ester group containing compounds, an acceleration of the splitting can also be achieved by addition of pancreatin.

The additive used in accordance with the invention which are alkali-cleavable halogen organic compounds have the ability just as do the esters of neutralizing alkali. For use herein there can be used many different halogen compounds as for example ethyl chloroacetate ethylester which additive additionally has the ability to react with mercapto compounds and to thereby lower their concentration in the preparation. According to the process of the invention the following compounds may be effectively used: ethyl acetate, diethyl malonate, ethylene glycol monostearate, ethyl lactate monoacetin, diacetin, triacetin, 2-methoxyethyl acetate, gammabutyrolactone, 1,2-ethanediol carbonate (1,3- dioxolan-2-one), glycol sulfite, methyl chloroacetate, ethyl chloroacetate, 2-chloroethanol, 1-chloro-2-propanol, cyanuric chloride (trichloro-s-triazine), chloroacetamide, chlorobutanol, chloroacetylurea, ethyl pyruvate, triethyl citrate and the like.

The process and agent of the invention have as compared to the known alkali reactive cosmetic preparations when used at the same strength, the advantage that they are possessed of an essentially improved compatibility for the skin and hair.

The following Examples are given in order to more clearly illustrate the invention and are in noways to be construed as in any way limiting the scope thereof.

EXAMPLE 1

Hair colorant

| | |
|---|---|
| 20.0 g | cetylalcohol |
| 2.0 g | sodiumcetylalcoholsulfate |
| 5.0 g | wool wax |
| 0.3 g | p-toluylenediamine |
| 0.08 g | resorcinol |
| 0.01 g | m-aminophenol |
| 9.1 g | ammonia (25%) |
| 63.51 g | water |
| 100.00 g | |

50 g Of the above set out alkaline reactive hair colorant were shortly before use mixed with 4.5 g ethyl lactate and 50 ml hydrogen peroxide solution (6–18%). This mixture was applied onto the hair to be colored. After a 30 minute working period during which the alkali concentration was decreased by about 30%, the hair was rinsed and dried. There was obtained in this manner a very well adjusted, i.e., compensated natural appearing blond tone with optimal preservation of the structure of the hair.

EXAMPLE 2

Hair colorant

| | |
|---|---|
| 35.0 g | oleic acid |
| 15.0 g | isopropylalcohol |
| 18.0 g | ammonia (25%) |
| 0.2 g | disodium salt of ethylenediaminetetraaceticacid |
| 0.1 g | sodium sulfite |
| 0.8 g | p-toluylenediamine |
| 0.2 g | resorcinol |
| 0.05 g | m-aminophenol |
| 30.65 g | water |
| 100.00 g | |

50 ml Of the above-described alkaline reacting hair colorant were shortly before use, mixed with 10 g ethyl pyruvate and 50 ml hydrogen peroxide solution (6%). After a working time of 30 minutes, during which time, the alkali and also the hydrogen peroxide solution concentration were decreased by about 30%, the colorant was rinsed out and the hair dried. The hair thus treated had at optimal preservation of its structure an excellently compensated blond tone.

EXAMPLE 3

Hair straightening agent

| | |
|---|---|
| 5.4 g | cetylalcohol |
| 1.8 g | paraffin oil |
| 3.9 g | oleylalcohol oxyethylated with 20 mol ethyleneoxide |
| 1.5 g | colloidal silicic acid |
| 16.6 g | aqeuous ammonium thioglycolate solution (50%) |
| 5.6 g | ammonia (25%) |
| 0.3 g | perfume oil |
| 64.9 g | water |

-continued

Hair straightening agent

| | |
|---|---|
| 100.00 g | |

The above-described cream had a pH of 9.5 and contained 1.4% ammonia as well as 8.3% ammonium thioglycolate. This agent was employed in the conventional manner, that is the process of the invention was not followed and when used on the hair the preparation retained its activity unchanged.

When, however, shortly before its use there was added to the preparation, 4 g ethyl chloroacetate or a powder-form mixture of 4 g ethyl chloroacetate and 1 g colloidal silicic acid and the agent then used in this form on the hair, there occurred a gradual decrease of the active agent content with the result that at 30°C after 20 minutes the following decreases were noted:

free alkali — about 57%
thioglycolate — about 30%

If another additive in accordance with the invention was used or if alternatively the amount of additive was changed there can be realized any desired decrease in the concentration of the active agent. Thus for example if there is added to the foregoing hair straightening agent shortly before its use, 6.4 g triacetin (glycerinetriacetate) there is obtained at 30°C the following decreases in alkali amount:

after 20 minutes — about 18%
after 40 minutes — about 27%

EXAMPLE 4

Hair straightening agent

| | |
|---|---|
| 3.0 g | sodium hydroxide |
| 5.0 g | tragacanth |
| 0.5 g | perfume oil |
| 91.5 g | water |
| 100.00 g | |

When used on the hair, this agent works to effect an increasing softening of the hair at is maximum strength from start to finish of the process.

If, however, shortly before use, 3 g 2-chloroethanol are admixed therewith and the preparation then used on the hair in the conventional manner, then the alkalinity decreases after 10 minutes by about 26%, after 20 minutes by about 32%, after 30 minutes by about 39% measured from the original alkalinity. In this way, damage to the hair and the skin can be extensively avoided.

EXAMPLE 5

Hair shaping composition

| | |
|---|---|
| 21.8 g | aqueous ammonium thioglycolate solution (50%) |
| 4.0 g | ammonia (25%) |
| 0.3 g | perfume oil |
| 0.3 g | octylphenol oxyethylated with 20 mol ethyleneoxide |
| 73.6 g | water |
| 100.00 g | |

The aforesaid composition has a pH of 9.4 and contains 1% ammonia as well as 10.9% ammonium thioglycolate. Shortly before use, there is added to this composition 6 g gamma-butyrolactone and the composition then used as is conventional for a permanent waving or straightening agent. At 30°C, the decrease amounts to about 18% (after 20 minutes) and to 26% (after 40 minutes) in alkali content.

The gamma-butyrolactone can be added in the case of a conventional permanent waving treatment to a portion of the waving solution before its use and then in a separate step this solution applied onto the hair which has been prewet with the solution as originally described. There is used for this purpose 50 ml of this solution, 4.5 g of the lactone.

EXAMPLE 6

Fixing agent for use after hair shaping
6.2 g sodium peroxide carbonate ($2Na_2CO_3.3H_2O_2$)
3.0 g sodium lauryl sulfate
0.5 g perfume oil
1.0 g colloidal silicic acid The above powder is dissolved shortly before use in 100 ml water, treated with 10 ml methyl chloroacetate and then used in the conventional manner. The starting pH of 10.3 of the fixing agent falls gradually during the working period and namely amounts after 5 minutes at a temperature of about 30°C to a value of 8.2 and after 10 minutes to 7.4. The agent has at the start, a strong oxidative effect on the hair which over the working period becomes gradually weaker.

EXAMPLE 7

Permanent waving agent

| | |
|---|---|
| 17.5 g | aqueous ammonium thioglycolate solution (50%) |
| 6.6 g | ammonia (25%) |
| 0.5 g | perfume oil |
| 1.0 g | octylphenol oxyethylated with 20 mol ethyleneoxide |
| 74.4 g | water |
| 100.00 g | |

The above-described waving liquid has a pH of 9.5 and contains 1.65% ammonia as well as 8.7% ammonium thioglycolate. The hair is moistened with this waving liquid in the conventional manner, wound up on rollers and the solution allowed to act thereon for 15 to 20 minutes.

Because of the increasing softening of the hair which takes place, the activity of the waving solution with the passage of time is much too intensive.

If, however, shortly before use, to 80 ml of the waving liquid, there are added 5.6 g ethyl chloroacetate and then the agent is applied onto the hair in the conventional manner, the alkali content is decreased because of the ester saponification which takes place, amounting after 20 minutes to about 15% and after 40 minutes to about 22%.

One can, in accordance with the invention, add the ethyl chloroacetate in case of the conventional permanent waving treatment as has been described above in its entirety to the waving solution or shortly before its use to a portion thereof which is then applied onto the hair after it has been wet through with the above-described permanent waving solution. In this connection there can be added to 40 ml of waving liquid, 4.2 g of the ester and 1 g pancreatin and then the resultant agent used to after-wet the wound-up hair.

EXAMPLE 8

Cuticle remover

| | |
|---|---|
| 3.0 g | sodium hydroxide |
| 1.0 g | sodium laurylsulfate |
| 9.0 g | cetyl alcohol |
| 0.2 g | perfume oil |
| 86.8 g | water |
| 100.00 g | |

To 10 g of the above-described cream, there is added shortly before its use 0.5 g ethyl propionate. During the treatment the action of the agent is gradually decreased so that there results diminished risks of injury or damage to the skin through careless use of the agent.

EXAMPLE 9

Skin treating agent
(for removing dry, horny lamella (plates) on the skin's surface)

| | |
|---|---|
| 2.0 g | monoethanolamine salt of thiolactic acid |
| 0.5 g | monoethanolamine |
| 0.5 g | perfume oil |
| 5.0 g | tragacanth |
| 92.0 g | water |
| 100.00 g | |

Shortly before use, 20 g of this cream has added thereto a mixture consisting of 0.2 g diacetin, 0.2 g perfume oil, and 0.3 g oleyl alcohol oxyethylated with 20 mol ethyleneoxide. The preparation is then used conventionally, the activity of the active components being gradually decreased over the period of use.

We claim:

1. In a method for the treatment of live hair which comprises applying thereto a conventional alkaline composition that is adapted for permanently waving, shaping, or straightening live hair, the improvement which comprises adding to the said composition before it is applied to live hair an agent which gradually reduces the alkalinity of the said composition, the said agent being selected from the group consisting of 2-chloroethanol, 1-chloro-2-propanol, chlorobutanol, ethyl acetate, ethyl propionate 2-methoxyethyl acetate, methyl chloroacetate, ethyl chloroacetate, ethyl lactate, ethyl pyruvate, diethyl malonate, 1,3-dioxolan-2-one, triethyl citrate, ethylene glycol monostearate, monoacetin, diacetin, triacetin, gammabutyrolactone, chloroacetamide, chloroacetylurea, cyanuric chloride, and glycol sulfite.

2. The method of claim 1 in which the agent is added to the composition in an amount between 1 and 10% weight of the composition.

3. The method of claim 1 in which the conventional alkaline composition for treating live hair further contains at least one member selected from the group consisting of perfume oils, wetting agents, solvents, adsorption agents, thickeners, and dyestuffs.

4. The method of claim 3 in which the adsorption agent is colloidal silicic acid.

5. The method of claim 1 in which the live-hair-treating composition is a live-hair-shaping composition and the agent that is added thereto before the composition is applied to the hair is gammabutyrolactone.

6. The method of claim 5 in which the live-hair-shaping composition comprises ammonium thioglycolate and ammonia.

* * * * *